US00PP27999P2

(12) United States Plant Patent
Danziger

(10) Patent No.: US PP27,999 P2
(45) Date of Patent: May 9, 2017

(54) ***PETUNIA* PLANT NAMED 'DCASPITAYA'**

(50) Latin Name: ***Petunia* hybrid**
Varietal Denomination: DCASPITAYA

(71) Applicant: Gavriel Danziger, Moshav Mishmar Hashiva (IL)

(72) Inventor: Gavriel Danziger, Moshav Mishmar Hashiva (IL)

(73) Assignee: Danziger 'DAN' Flower Farm (IL)

( * ) Notice: Subject to any disclaimer, the term of this patent is extended or adjusted under 35 U.S.C. 154(b) by 0 days.

(21) Appl. No.: 14/757,330

(22) Filed: Dec. 16, 2015

(51) Int. Cl.
*A01H 5/02* (2006.01)

(52) U.S. Cl.
USPC ..... Plt./356.18

(58) Field of Classification Search
USPC ..... Plt./356.18
CPC ..... A01H 5/02
See application file for complete search history.

*Primary Examiner* — Kent L Bell
(74) *Attorney, Agent, or Firm* — Cassandra Bright

(57) ABSTRACT

A new and distinct *Petunia* cultivar named 'DCASPITAYA' is disclosed, characterized by a semi-trailing growth habit, well-branched plant form, strong vigor and an abundance of large purple flowers with yellow-green margins and dark violet veins and throat. The new variety is a *Petunia*, normally produced as an outdoor garden or container plant.

2 Drawing Sheets

Figure 1:
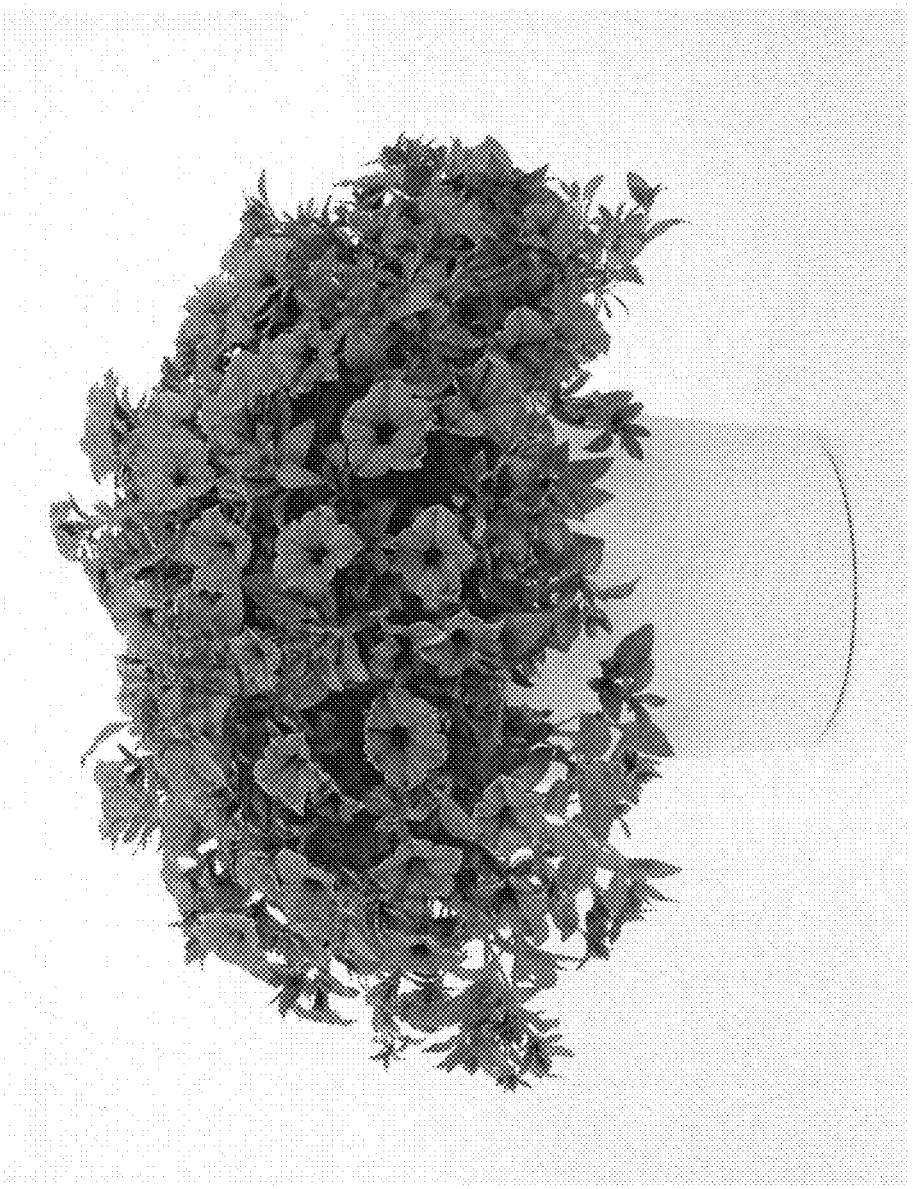

Latin name of the genus and species: *Petunia* hybrid.
Variety denomination: 'DCASPITAYA'.

BACKGROUND OF THE INVENTION

The new *Petunia* cultivar is a product of a planned breeding program conducted by the inventor, Gavriel Danziger, in Mishmar Hashiva, Israel. The objective of the breeding program was to produce new *Petunia* varieties for ornamental commercial applications. The cross resulting in this new variety was made during January 2013.

The seed parent is the unpatented, proprietary variety referred to as *Petunia* 'cv. 11-5032'. The pollen parent is the unpatented, propriety variety referred to as *Petunia* 'cv. 11-5030'. The new variety was discovered in September 2013 by the inventor in a group of seedlings resulting from the January 2013 crossing, in a research greenhouse in Mishmar Hashiva, Israel.

Asexual reproduction of the new cultivar was performed by terminal vegetative cuttings. This was first performed at a research greenhouse in Mishmar Hashiva, Israel in September 2013 and has shown that the unique features of this cultivar are stable and reproduced true to type in more than 25 successive generations.

SUMMARY OF THE INVENTION

The cultivar 'DCASPITAYA' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DCASPITAYA' These characteristics in combination distinguish 'DCASPITAYA' as a new and distinct *Petunia* cultivar:

1. Semi-trailing growth habit
2. Very well branched plant with strong vigor

3. Flower color is Purple with Yellow-Green margins and dark Violet veins and throat
4. Flower size is large.
5. Abundant flowering.

Plants of the new cultivar 'DCASPITAYA' are similar to plants of the seed (female) parent (the unpatented 'cv. 11-5032') in most horticultural characteristics, however, plants of the new cultivar 'DCASPITAYA' differ in the following;

1. The new variety has a semi-trailing plant habit, seed parent has a trailing growth habit
2. The new variety is more vigorous and produces more branches per plant than the parent variety.
3. Flower color of the new variety is Purple with Violet veins and a Yellow-Green margin. Flower color of the parent plant is White with Purple veins and Green margins.
4. The new variety flowers more abundantly than the seed parent variety.

Plants of the new cultivar 'DCASPITAYA' are similar to plants of the pollen (male) parent (unpatented 'cv. 11-5030') in most horticultural characteristics, however, plants of the new cultivar 'DCASPITAYA' differ in the following;

1. Flower color of the new variety is Purple with Violet veins and a Yellow-Green margin. Flower color of the pollen parent is Purple.

COMMERCIAL COMPARISON

Plants of the new cultivar 'DCASPITAYA' are comparable to the commercial variety *Petunia* 'DCAS301', U.S. Plant Pat. No. 27,238. The two *Petunia* varieties are similar in most horticultural characteristics; however, the new variety 'DCASPITAYA' differs in the following:

1. Flower size of the new variety is larger than the flower size of this comparator.

2. The new variety has Purple flowers with dark Violet veins and throat and Yellow-Green margins. Comparator flower color is Purple with a White Rim.
3. Over all flower shape of the new variety is somewhat star-shaped, with acute petal aspices. Overall flower shape of this comparator is rounded.
4. Foliage of the new variety is larger than foliage of this comparator.

Plants of the new cultivar 'DCASPITAYA' can also be compared to the unpatented commercial variety *Petunia* 'DANRAY3'. The two *Petunia* varieties are similar in most horticultural characteristics; however, the new variety 'DCASPITAYA' differs in the following:

1. The new variety has a smaller flower than this comparator.
2. The new variety has Purple flowers with dark Violet veins and throat and Yellow-Green margins. Comparator flower color is Light Purple with dark Purple veins.
3. The new variety has a semi-trailing growth habit. This comparator has a mounded plant habit.
4. Over all flower shape of the new variety is somewhat star-shaped, with acute petal aspices. Overall flower shape of this comparator is rounded.

BRIEF DESCRIPTION OF THE PHOTOGRAPHS

The accompanying photograph in FIG. 1 illustrates in full color a typical plant of 'DCASPITAYA' grown in a nursery, in a 13 cm pot. Age of the plant photographed is approximately 90 days from a rooted cutting.

Figure 2:
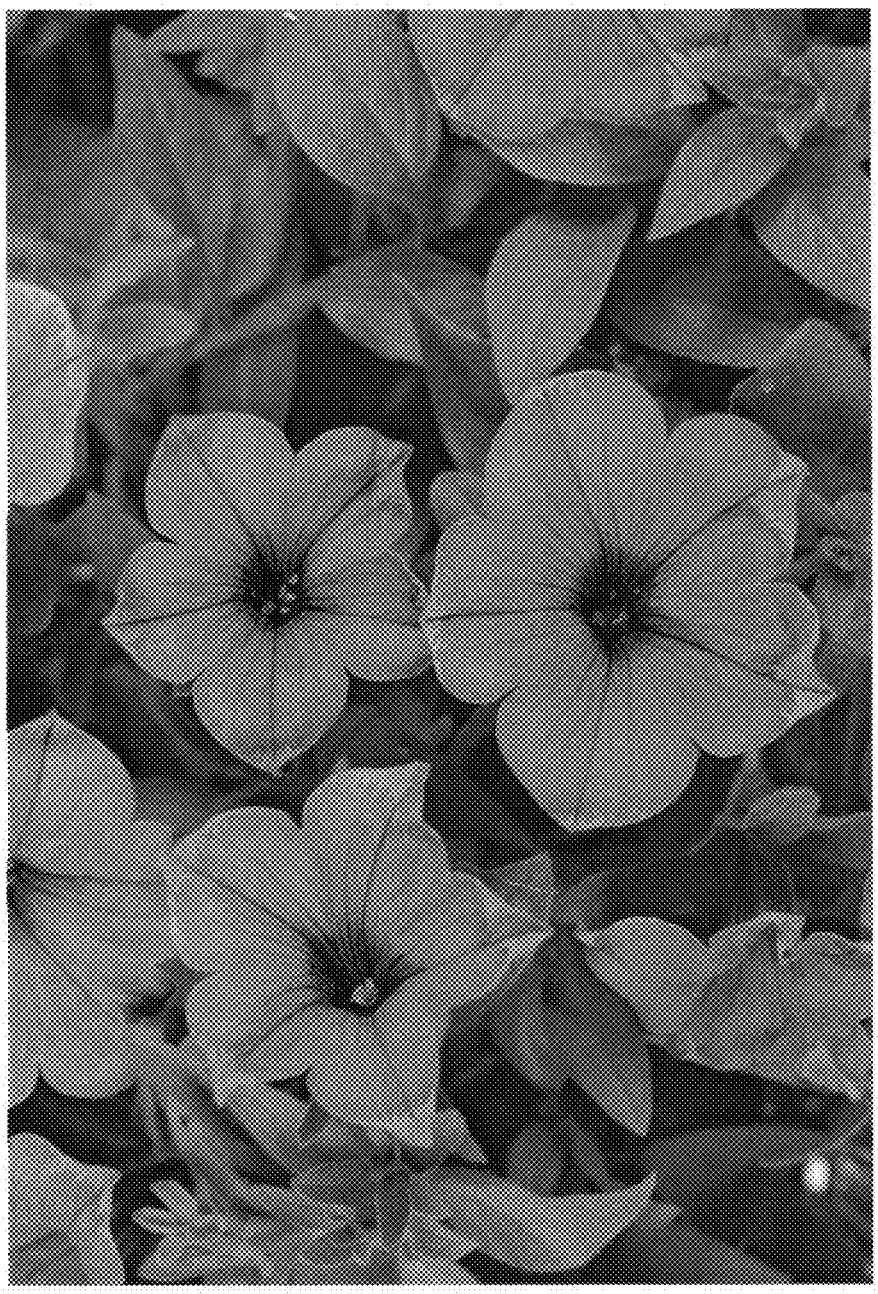

FIG. 2 illustrates a close up of the flowers and foliage.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2001 except where general terms of ordinary dictionary significance are used. The following observations and measurements describe 'DCASPITAYA' plants grown outdoors and in greenhouse during the Spring, Summer and Autumn, in Mishmar Hashiva, Israel. The growing temperature ranged from 20° C. to 35° C. during the day and from 17° C. to 23° C. during the night. General light conditions are bright, normal sunlight. Measurements and numerical values represent averages of typical plant types.

Botanical classification: *Petunia* 'DCASPITAYA'.

PROPAGATION

Type of propagation typically used: Vegetative terminal cuttings.

Time to initiate roots: 10 to 14 days at approximately 20° C.

Root description: Fibrous.

PLANT

Age of plant described: Approximately 60 days from a rooted cutting.

Pot size of plant described: 13 cm.

Growth habit: Semi-trailing.

Height: Approximately 22 cm.

Plant spread: Approximately 55 cm.

Growth rate: Strong.

Branching characteristics: Well-branched.

Characteristics of primary lateral branches:

*Quantity of primary lateral branches.*—8.

*Length of primary lateral branches.*—Approximately 35 cm.

*Form.*—Cylindrical.

*Diameter.*—Approximately 0.4 cm.

*Color.*—RHS Yellow-Green 144A.

*Texture.*—Pubescent.

*Strength.*—Strong, flexible.

Internode length: 2.5 cm.

FOLIAGE

Leaf:

*Arrangement.*—Opposite.

*Quantity.*—Approximately 30 per branch.

*Average length.*—7 cm.

*Average width.*—3 cm.

*Shape of blade.*—Elliptical.

*Apex.*—Acute.

*Base.*—Acute.

*Margin.*—Entire.

*Texture of top surface.*—Velvety.

*Texture of bottom surface.*—Velvety.

*Pubescence.*—Soft, short pubescence upper and lower surfaces.

*Color.*—Young foliage upper side: RHS Yellow-Green 146B. Young foliage under side: RHS Yellow-Green 146C. Mature foliage upper side: RHS Yellow-Green 146A. Mature foliage under side: RHS Yellow-Green 146B.

*Venation.*—Type: Pinnate. Venation color upper side: RHS Yellow-Green 146C. Venation color under side: RHS Yellow-Green 146D.

*Petiole.*—Length: 1 cm. Diameter: 0.3 cm. Color: RHS Yellow-Green 146B. Texture: Velvety.

FLOWER

Natural flowering season: Spring, Summer, and Autumn in Mishmar Hashiva, Israel.

Days to flowering from rooted cutting: Approximately 30 days.

Inflorescence and flower type and habit: Axillary, single flower, salverform shape, erect habit.

Rate of flower opening: 2 to 3 days from bud to fully opened flower.

Flower longevity on plant: 3 to 6 days.

Approximate quantity of flowers per plant: Approximately 70.

Persistent or self-cleaning: Self-cleaning.

Bud:

*Shape.*—Tubular.

*Length.*—4 cm.

*Diameter.*—Approximately 0.7 cm.

*Color.*—RHS Purple N79A with green margins near RHS Yellow-Green 144A.

Flower size:

*Diameter.*—Approximately 6.5 cm.

*Length.*—Approximately 3.0 cm.

*Flower tube diameter at distal end.*—Approximately 1.5 cm.

*Flower tube diameter at proximal end.*—Approximately 0.4 cm.

Petals:

*Length from throat.*—Approximately 2.5 cm.

*Width.*—Approximately 3.0 cm.

*Quantity.*—5.

*Texture.*—Velvety.

*Apex.*—Acute.

*Base.*—Fused.

*Margin.*—Wavy.

Color:

*When opening.*—Upper surface: Near RHS Red-Purple N78A. Veins near RHS Violet 86A. Margins RHS Yellow-Green 144A. Lower surface: Near RHS Red-Purple N78B. Veins near RHS Violet 83A. Margins RHS Yellow-Green 144B.

*Fully opened.*—Upper surface: Near RHS Red-Purple N78A. Veins Violet RHS Violet 86A. Margins RHS Yellow-Green 144A. Throat rim color: RHS Greyed-Purple 187A. Lower surface: Near RHS Red-Purple N78B. Veins near RHS Violet 83A. Margins near RHS Yellow-Green 144B. Flower throat (inside): Near RHS Violet 86B. Flower throat, vein: Near RHS Violet 86A. Flower tube (outside): Near RHS Purple 79A. Flower tube, vein: Near RHS Purple 79A.

*Fading.*—Petals fading to: Near RHS Purple-Violet N81B. Veins near RHS Violet 83B. Margins RHS Yellow-Green 143B.

Calyx/sepals:

*Quantity per flower.*—5.

*Shape.*—Linear.

*Length.*—Approximately 2 cm.

*Width.*—Approximately 0.7 cm.

*Apex.*—Acute.

*Base.*—Fused.

*Margin.*—Entire.

*Texture.*—Velvety.

*Color.*—Upper Surface: RHS Yellow-Green 146A. Lower Surface: RHS Yellow-Green 146B.

Peduncle: Not present.

Pedicel:

*Length.*—Approximately 2 cm.

*Diameter.*—Approximately 0.2 cm.

*Color.*—RHS Yellow-Green 146B.

*Orientation.*—Straight, approximately 45 degrees from stem.

Fragrance: None.

REPRODUCTIVE ORGANS

Stamens:

*Number (per flower).*—5.

*Filament length.*—Approximately 2 cm.

Anthers:

*Shape.*—Rounded.

*Length.*—Approximately 0.1 cm.

*Color.*—RHS Yellow-White 158B.

Pollen:

*Color.*—RHS Yellow-White 158C.

*Amount.*—Scant.

Pistils:

*Quantity per flower.*—1.

*Length.*—Approximately 1.9 cm.

*Style.*—Length: Approximately 12.2 cm.

*Color.*—RHS Yellow-Green 144D.

*Stigma.*—Shape: Rounded. Color: RHS Yellow-Green 144C. Ovary Color: RHS Yellow-Green 144B.

OTHER CHARACTERISTICS

Seeds and fruits: Approximately 30 Black, rounded seeds of Approximately 0.5 mm diameter, per one brown, conical capsule. Minute, color values not accurately measured with the RHS chart.

Disease/pest resistance: Neither resistance nor susceptibility to the normal diseases and pests of *Petunia* have been observed. Typical well known diseases include: *Botrytis cineria, Fusarium, Pythium, Phytophthora*, and *Rhizoctonia* species. Typical well known pests include: Leaf miners, spider mites, thrips and possibly caterpillars.

Temperature tolerance: Tolerates a range between 5° C. to 40° C.

What is claimed is:

1. A new and distinct cultivar of *Petunia* plant named 'DCASPITAYA' as herein illustrated and described.

* * * * *